United States Patent
Nakatsuka et al.

(10) Patent No.: US 7,615,582 B2
(45) Date of Patent: Nov. 10, 2009

(54) ONE-PACK TYPE ADHESIVE COMPOSITION FOR DENTAL USE

(75) Inventors: Kazumitsu Nakatsuka, Tokyo (JP); Naoki Nishigaki, Kurashiki (JP)

(73) Assignee: Kuraray Medical Inc., Kurashiki-shi (JP)

( * ) Notice: Subject to any disclaimer, the term of this patent is extended or adjusted under 35 U.S.C. 154(b) by 504 days.

(21) Appl. No.: 10/582,958

(22) PCT Filed: Dec. 8, 2004

(86) PCT No.: PCT/JP2004/018272

§ 371 (c)(1), (2), (4) Date: Jun. 15, 2006

(87) PCT Pub. No.: WO2005/060920

PCT Pub. Date: Jul. 7, 2005

(65) Prior Publication Data

US 2007/0100020 A1     May 3, 2007

(30) Foreign Application Priority Data

Dec. 19, 2003    (JP)  ............................ 2003-423790

(51) Int. Cl.
     *A61C 13/23*       (2006.01)
     *A61C 13/225*     (2006.01)
     *A61C 13/00*      (2006.01)
     *A61K 6/00*        (2006.01)
     *C08F 2/50*        (2006.01)
     *C08J 3/28*         (2006.01)

(52) U.S. Cl. ........................... 522/171; 522/71; 522/74; 522/84; 522/86; 522/79; 522/150; 522/151; 522/153; 522/173; 522/178; 522/182; 522/908; 523/105; 523/109; 523/111; 523/112; 523/113; 523/114; 523/115; 523/116; 523/118; 523/120; 526/277; 526/274; 526/286; 526/287; 526/318.2; 526/318.3; 524/800; 524/804; 524/807; 524/816; 524/821; 524/820; 524/823; 524/845

(58) Field of Classification Search .................... 522/71, 522/74, 79, 150, 151, 153, 171, 173, 178, 522/182, 908, 84, 86; 523/105, 109, 111, 523/112, 113, 114, 115, 116, 118, 120; 526/277, 526/274, 286, 287, 318.2, 318.3; 524/800, 524/804, 807, 816, 821, 820, 823, 845
See application file for complete search history.

(56) References Cited

FOREIGN PATENT DOCUMENTS

| JP | 62 223289 | 10/1987 |
|----|-----------|---------|
| JP | 3 240712 | 10/1991 |
| JP | 7 97306 | 4/1995 |
| JP | 2001 49199 | 2/2001 |
| JP | 2003 73218 | 3/2003 |
| JP | 2004 352698 | 2/2004 |

OTHER PUBLICATIONS

U.S. Appl. No. 11/911,849, filed Oct. 18, 2007, Nakatsuka, et al.

*Primary Examiner*—Sanza L McClendon
(74) *Attorney, Agent, or Firm*—Oblon, Spivak, McClelland, Maier & Neustadt, L.L.P.

(57) ABSTRACT

A hydrophobic acidic group-containing polymeric monomer (a); a water-soluble polymeric monomer (b); water (c); a photopolymerization initiator (d); an aromatic tertiary amine (e) having an electron-withdrawing group; a cross-linkable polymeric monomer (f); and a basic compound (g) for producing a water-soluble salt through a reaction with a part of the hydrophobic acidic group-containing polymeric monomer (a) are included as essential compounding ingredients.

A one-part dental adhesive composition that exhibits high adhesive strength and high storage stability in adhesion between a teeth, and more particularly enamel or dentine, and a dental repairing material, and more particularly a resin material, is provided. Since the adhesive composition is one-part type, there is no need to mix in an adhering operation, and in addition, it exhibits high adhesive strength without performing preprocessing (etching processing and priming processing), it is suitably used as a one-step type dental adhesive composition for performing an adhering operation in a teeth repairing treatment in one processing.

8 Claims, No Drawings

ONE-PACK TYPE ADHESIVE COMPOSITION FOR DENTAL USE

TECHNICAL FIELD

The present invention relates to a one-part dental adhesive composition, and more particularly, it relates to a one-part dental adhesive composition used for adhering a dental repairing material such as a dental composite resin, a dental compomer or a dental resin cement onto a tooth hard structure (dentine).

BACKGROUND ART

For repairing a dentine (enamel, dentine and cement) damaged through dental caries or the like, a filling repairing material such as a filling composite resin or a filling compomer or a crown repairing material such as a metal alloy, a porcelain or a resin material is generally used. However, a filling repairing material or a crown repairing material (herein sometimes generically designated as a "dental repairing material") itself does not have an adhesive property onto a dentine. Therefore, a variety of adhesive systems using adhesives are conventionally used for adhering a dental repairing material onto a dentine. A conventional general adhesive system is what is called an acid etching type adhesive system in which the surface of a dentine is etched with an acid etching agent such as a phosphoric acid aqueous solution before applying a bonding agent, that is, an adhesive, to the dentine for adhering a dental repairing material onto the dentine.

Recently, what is called a self-etching type adhesive system is proposed as an adhesive system using no acid etching agent (see, for example, Patent Documents 1 and 2 below). In this adhesive system, after coating the surface of a dentine with a self-etching primer including an acidic monomer and a hydrophilic monomer, a bonding agent is applied to the dentine without rinsing the dentine. Also, another adhesive system in which after coating a dentine with an adhesive composition (self-etching primer) including a water-insoluble acidic monomer, a basic compound and water, a bonding agent is applied to the dentine without rinsing (see, for example, Patent Document 3 below).

Recently, an adhesive system using a dental adhesive composition having a function as a self-etching primer in addition to the original function as a bonding agent (which type of dental adhesive composition having no need of preprocessing (i.e., etching processing and priming processing) is hereinafter sometimes referred to as a one-step type dental adhesive composition) is proposed (see, for example, Patent Document 4 below). A one-step type dental adhesive composition described in Patent Document 4 is a dental adhesive composition including, in a given ratio, a polymeric monomer having a phosphoric group, a polymeric monomer having a plurality of carboxyl groups in one molecule or a polymeric monomer that produces a plurality of carboxyl groups in one molecule through a reaction with water, a polymeric monomer having no acid group (acidic group) and having solubility in water at 20° C. of 25 wt % or less, water, a photopolymerization initiator and a viscosity modifier.

Patent Document 1: Japanese Laid-Open Patent Publication No. Sho 62-223289 (p. 8 and Table 1)
Patent Document 2: Japanese Laid-Open Patent Publication No. Hei 3-240712 (p. 8 and Table 1)
Patent Document 3: Japanese Laid-Open Patent Publication No. 2001-49199 ([0048] Embodiment 2)
Patent Document 4: Japanese Laid-Open Patent Publication No. 2003-73218 ([0024] Table 1)

DISCLOSURE OF INVENTION

Problems to be Solved by Invention

In general, a dental treatment is performed in an environment easily affected by saliva and blood, and therefore, it is necessary to simply and rapidly perform an adhering operation.

In the acid etching type adhesive system, however, it is necessary to perform two processing, that is, etching processing and bonding agent applying processing. Also, another rinsing and drying processing for removing the used acid etching agent should be additionally performed after the etching processing. Therefore, it is difficult to simply and rapidly perform the adhering operation. Also, in this adhesive system, a sufficient adhesive property can be attained on enamel but cannot be attained on dentine.

In the self-etching type adhesive system described in Patent Document 1 or 2, there is no need to perform the rinsing and drying processing because no acid etching agent is used. Furthermore, a sufficient adhesive property can be attained not only on enamel but also on dentine. In this adhesive system, however, it is necessary to perform two processing, that is, self-etching priming processing (simultaneous processing for etching and priming) and bonding agent applying processing. Therefore, it is difficult to simply and rapidly perform the adhering operation. In the case where an adhesive composition described in Patent Document 3 is used as a self-etching primer in a two-step type adhesive system in which a bonding agent is applied after applying a self-etching primer, a sufficient adhesive property can be attained. In the case where this adhesive composition is used as a one-step type dental adhesive, however, a high adhesive property equivalent to that attained in the two-step type adhesive system cannot be attained.

Since the dental adhesive composition described in Patent Document 4 is one-part type and one-step type, the adhering operation can be simply and rapidly performed. This dental adhesive composition has, however, the same problems as this type of dental adhesive composition currently commercially available, namely, problems that a sufficient adhesive property cannot be attained and that the adhesive property is easily varied by a small difference occurring in the adhering operation. Furthermore, this dental adhesive composition also has a problem of poor storage stability. Therefore, dentists and the like have earnestly desired development of a one-part dental adhesive composition with a practically sufficient adhesive strength and storage stability.

The present invention was devised for meeting the desire, and an object of the invention is providing a one-part dental adhesive composition that exhibits high adhesive strength in adhesion between a teeth, and specifically enamel and dentine, and a dental repairing material, and specifically a resin material, and has high storage stability.

Means for Solving Problems

The dental adhesive composition according to the present invention devised for achieving the object includes, as essential compounding ingredients, a hydrophobic acidic group-containing polymeric monomer (a); a water-soluble (hydrophilic) polymeric monomer (b); water (c); a photopolymerization initiator (d); aromatic tertiary amine (e) having an electron-withdrawing group; a cross-linkable polymeric monomer (f); and a basic compound (g) for producing a water-soluble salt through a reaction with a part of the hydrophobic acidic group-containing polymeric monomer (a).

Effect of Invention

The present invention provides a one-part dental adhesive composition that exhibits high adhesive strength in adhesion between a teeth, and more particularly enamel or dentine, and a dental repairing material, and more particularly a resin material, and has high storage stability. Since the one-part dental adhesive composition of the invention is a one-part type, mixing is not necessary in an adhering operation, and in addition, it exhibits high adhesive strength without preprocessing (etching processing and priming processing). Therefore, it can be suitably used as a one-step type dental adhesive composition for performing an adhering operation in a teeth repairing treatment in one processing.

Preferred Embodiments

The hydrophobic acidic group-containing polymeric monomer (a) used in the present invention has solubility less than 10 wt % in water at 25° C. The solubility is preferably less than 5 wt % and most preferably less than 1 wt %. The hydrophobic acidic group-containing polymeric monomer (a) permeates a dentine while decalcifying to bond to the dentine. In the present invention, the hydrophobic acidic group-containing polymeric monomer (a) is used instead of a water-soluble acidic group-containing polymeric monomer for the following reason: Although the water-soluble acidic group-containing polymeric monomer has higher permeability into a dentine than the hydrophobic acidic group-containing polymeric monomer (a), it cannot attain high adhesion durability (long-lasting adhesion) because it is water-soluble and hence poor at water resistance obtained after polymeric curing. Although a salt, that is, a reaction product produced from the hydrophobic acidic group-containing polymeric monomer (a) and the basic compound (g) in this invention, is water-soluble, the salt reacts with apatite of the dentine so as to ultimately produce a water-insoluble Ca salt, and hence high adhesion durability is attained. The hydrophobic acidic group-containing polymeric monomer (a) is a polymeric monomer including at least one acidic group, such as a univalent phosphoric group [a phosphinico group: =P(=O)OH], a bivalent phosphoric group [a phosphono group: —P(=O)(OH)$_2$], a pyrophosphoric group [—P(=O)(OH)—O—P(=O)(OH)—], a carboxylic group [a carboxyl group: —C(=O)OH, an anhydride group: —C(=O)—O—(=O)—] or a sulfonic group [a sulfo group: —SO$_3$H, —OSO$_3$H], and at least one polymeric group (a polymerizable unsaturated group), such as an acryloyl group, a methacryloyl group, a vinyl group or a vinylbenzyl group. Specific examples are as follows, wherein methacryloyl and acryloyl are sometimes comprehensively mentioned as (meth)acryloyl:

Examples of a hydrophobic phosphoric group-containing polymeric monomer (a-1) are 6-(meth)acryloyloxyhexyl dihydrogenphosphate, 7-(meth)acryloyloxyheptyl dihydrogenphosphate, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, bis[6-(meth)acryloyloxyhexyl]hydrogenphosphate, bis[8-(meth)acryloyloxyoctyl]hydrogenphosphate, bis[9-(meth)acryloyloxynonyl]hydrogenphosphate, bis[10-(meth)acryloyloxydecyl]hydrogenphosphate, 1,3-di(meth)acryloyloxypropyl dihydrogenphosphate, 2-(meth)acryloyloxyethylphenyl hydrogenphosphate, 2-(meth)acryloyloxyethyl-2-bromoethyl hydrogenphosphate, (5-methacryloxy)pentyl-3-phosphonopropionate, (6-methacryloxy)hexyl-3-phosphonopropionate, (10-methacryloxy)decyl-3-phosphonopropionate, (6-methacyloxy)hexyl-3-phosphonoacetate, (10-methacryloxy)decyl-3-phosphonoacetate, 2-methacryloyloxyethyl (4-methoxyphenyl) hydrogenphosphate and 2-methacryloyloxypropyl (4-methoxyphenyl) hydrogenphosphate.

Examples of a hydrophobic pyrophosphoric group-containing polymeric monomer (a-2) are bis[6-(meth)acryloyloxyhexyl]pyrophosphate, bis[8-(meth)acryloyloxyoctyl]pyrophosphate and bis[10-(meth)acryloyloxydecyl]pyrophosphate.

Examples of a hydrophobic carboxylic group-containing polymeric monomer (a-3) are 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and their acid anhydrides, 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid and 11-(meth)acryloyloxy-1,1-undecanedicarboxylic acid.

Examples of a hydrophobic sulfonic group-containing polymeric monomer (a-4) are styrene sulfonic acid, 6-sulfohexyl (meth)acrylate and 10-sulfodecyl (meth)acrylate.

Among the aforementioned hydrophobic acidic group-containing polymeric monomers (a-1) through (a-4), a (meth)acrylate-based polymeric monomer including, in a molecule, at least one univalent phosphoric group [phosphonico group: —P(=O)(OH)—], bivalent phosphoric group [phosphono group: —P(=O)(OH)$_2$] or pyrophosphoric group [—P(=O)(OH)—O—P(=O)(OH)—] is preferred because of its high adhesive strength onto a teeth, and more particularly, a (meth)acrylate-based polymeric monomer including a bivalent phosphoric group [a phosphono group: —P(=O)(OH)$_2$] is preferred. In particular, a bivalent phosphoric group-containing polymeric monomer including, in a molecule, an alkyl group or an alkylene group with a carbon number of a main chain of 2 through 40 is more preferred, and a bivalent phosphoric group-containing polymeric monomer including, in a molecule, an alkylene group with a carbon number of a main chain of 8 through 12, such as 10-methacryloyloxydecyl dihydrogenphosphate, is most preferred.

One of these hydrophobic acidic group-containing polymeric monomers (a) may be singly used or a plurality of them may be mixedly used. The adhesive strength may be lowered when the hydrophobic acidic group-containing polymeric monomer (a) is deficiently or excessively included. The mixing ratio of the hydrophobic acidic group-containing polymeric monomer (a) is preferably 1 through 50 wt %, more preferably 1 through 40 wt % and most preferably 5 through 30 wt % based on a total weight of the dental adhesive composition.

The water-soluble polymeric monomer (b) used in the present invention has solubility in water at 25° C. of 10 wt % or more. A polymeric monomer with the solubility of 30 wt % or more is preferred, and one soluble in water at 25° C. in an arbitrary ratio is more preferred. The water-soluble polymeric monomer (b) accelerates the permeation, into a dentine, of the hydrophobic acidic group-containing polymeric monomer (a), the photopolymerization initiator (d), the aromatic tertiary amine (e) having an electron-withdrawing group, the cross-linkable polymeric monomer (f) and the basic compound (g), and itself permeates into the dentine to adhere onto an organic component (collagen) included in the dentine. Examples of the water-soluble polymeric monomer (b) are 2-hydroxyethyl (meth)acrylate, 3-hydroxypropyl (meth)acrylate, 2-hydroxypropyl (meth)acrylate, 3-hydroxypropyl (meth)acrylate, 1,3-dihydroxypropyl(meth)acrylate, 2,3-dihydroxypropyl(meth)acrylate, 2-trimethylammoniumethyl (meth)acryl chloride and polyethylene glycol di(meth)acrylate (having nine or more oxyethylene groups).

One of these water-soluble polymeric monomers (b) may be singly used or a plurality of them may be mixedly used. The adhesive strength may be lowered when the water-soluble polymeric monomer (b) is deficiently or excessively included. The mixing ratio of the water-soluble polymeric monomer (b) is preferably 1 through 60 wt %, more preferably 5 through 50 wt % and most preferably 10 through 40 wt % based on the total weight of the dental adhesive composition.

The water (c) used in the present invention accelerates the decalcification function of the hydrophobic acidic group-containing polymeric monomer (a) against a dentine. It is necessary to use water that includes substantially no impurity harmfully affecting the adhesive property. Distilled water or ion-exchanged water is preferably used. The adhesive strength may be lowered when the water (c) is deficiently or excessively included. The mixing ratio of the water (c) is preferably 1 through 50 wt %, more preferably 5 through 30 wt % and most preferably 10 through 20 wt % based on the total weight of the dental adhesive composition.

As the photopolymerization initiator (d) used in the present invention, any of known photopolymerization initiators can be used. Specific examples are α-diketones (d-1), ketals (d-2), thioxanthones (d-3), acylphosphine oxides (d-4) and coumarins (d-5). Among them, the acylphosphine oxides (d-4) are preferably used because they provide high adhesive strength to the dental adhesive composition. In the case where the dental adhesive composition of this invention is cured by using an irradiator using a blue LED, the α-diketones (d-1) such as camphorquinone are preferably used as the photopolymerization initiator because they provide a high curing property to the dental adhesive composition.

Examples of the α-diketones (d-1) are camphorquinone, benzyl and 2,3-pentanedione.

Examples of the ketals (d-2) are benzyl dimethyl ketal and benzyl diethyl ketal.

Examples of the thioxanthones (d-3) are 2-chlorothioxanthone and 2,4-diethylthioxanthone.

Examples of the acylphosphine oxides (d-4) are 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate and 2,4,6-trimethylbenzoylethoxyphenylphosphine oxide.

Examples of the coumarins (d-5) are 3,3'-carbonyl bis(7-diethylamino)coumarin, 3-(4-methoxybenzoyl) coumarin and 3-thienoylcoumarin.

One of these photopolymerization initiators (d) may be singly used or a plurality of them may be mixedly used. The mixing ratio of the photopolymerization initiator (d) is preferably 0.01 through 10 wt %, more preferably 0.1 through 7 wt % and most preferably 0.5 through 5 wt % based on the total weight of the dental adhesive composition.

The aromatic tertiary amine (e) having an electron-withdrawing group used in the present invention accelerates the curing function of the photopolymerization initiator (d). An example of the aromatic tertiary amine (e) having an electron-withdrawing group is a compound in which an electron-withdrawing group such as a carboxylic group, a carboxylate group, a nitrile group or a halogen group is substituted for a hydrogen atom of an aromatic ring of aromatic tertiary amine. In particular, compounds represented by Chemical Formula 1 below are preferred, and among the compounds represented by Chemical Formula 1, ethyl 4-N,N-dimethylaminobenzoate, methyl 4-N,N-dimethylaminobenzoate, propyl 4-N,N-dimethylaminobenzoate, n-butoxyethyl 4-N,N-dimethylaminobenzoate, 2-(methacryloyloxy)ethyl 4-N,N-dimethylaminobenzoate and 4-N,N-dimethylaminobenzophenone are more preferred.

Chemical Formula 1:

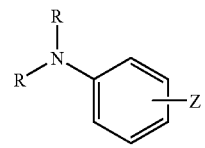

wherein

R: $-(CH_2)_n-CH_3$

[wherein n is an integer of 0 through 10.]

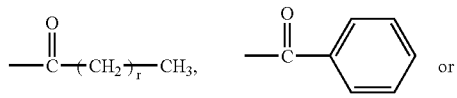

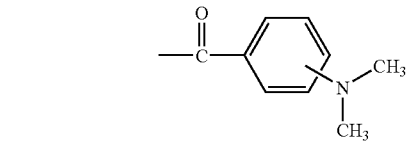

[wherein m is an integer of 0 through 10, p is an integer of 0 through 10, q is an integer of 0 through 10 and r is an integer of 0 through 10.]]

One of these aromatic tertiary amines (e) having an electron-withdrawing group may be singly used or a plurality of them may be mixedly used. The mixing ratio of the aromatic tertiary amine (e) having an electron-withdrawing group is preferably 0.01 through 10 wt %, more preferably 0.05 through 5 wt % and most preferably 0.1 through 2.5 wt % based on the total weight of the dental adhesive composition. When the mixing ratio of the aromatic tertiary amine (e) having an electron-withdrawing group is less than 0.01 wt % or exceeds 10 wt % based on the total weight of the dental adhesive composition, the adhesive strength may be lowered.

The cross-linkable polymeric monomer (D used in the present invention is a polymeric monomer including, in one molecule, at least two polymeric groups and no acidic group and having a hydrophobic property, namely, solubility less than 10 wt % in water at 25° C. The cross-linkable polymeric monomer (f) is strongly polymerized with the hydrophobic acidic group-containing polymeric monomer (a) and the water-soluble polymeric monomer (b) having a less polymeric curing property, so as to provide a high curing property (particularly, mechanical strength and water resistance) to the cured substance. Examples of the cross-linkable polymeric monomer (f) are bisphenol A diglycidyl (meth)acrylate (hereinafter referred to as "Bis-GMA"), 2,2-bis[4-(meth)acryloyloxyethoxyphenyl]propane, 2,2-bis[4-(meth)acryloyloxypolyethoxyphenyl]propane, [2,2,4-trimethylhexamethylene bis(2-carbamoyloxyethyl)dimethacrylate (hereinafter referred to as "UDMA"), ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate and compounds represented by Chemical Formulas 2, 3, 4, 5, 6 or 7 below. Among them, a compound including, in one molecule, at least three polymeric groups and a hydrocarbon group having at least six carbon atoms continuously bonded in a circular or linear shape is preferably used for attaining a high curing property.

Chemical Formula 2:

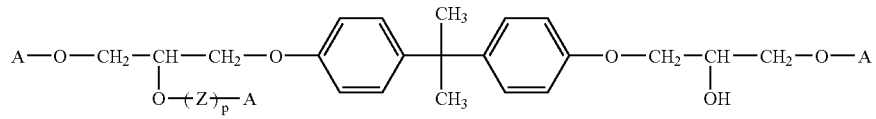

[wherein

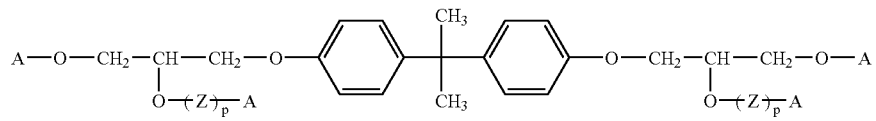

[wherein n is an integer of 1 through 20]p is 0 or 1.]

Chemical Formula 3:

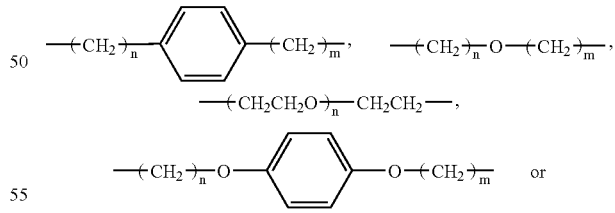

[wherein

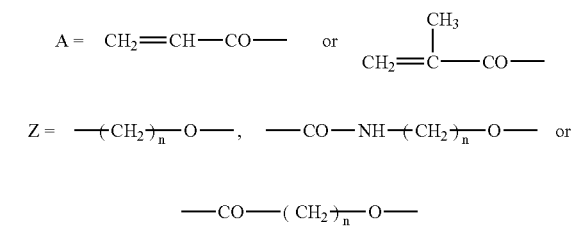

[wherein n is an integer of 1 through 20.] p is 0 or 1.]

Chemical Formula 4:

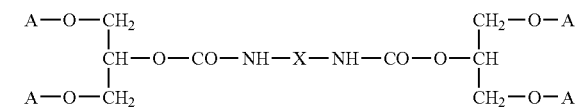

[wherein

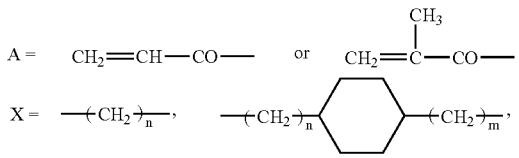

-continued

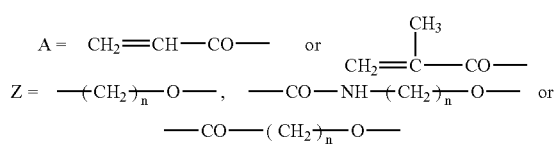

-continued

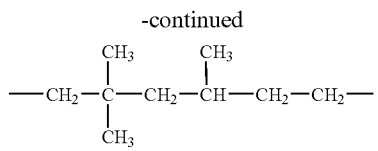

[wherein n is an integer of 1 through 20 and m is an integer of 1 through 20.]]

Chemical Formula 5:

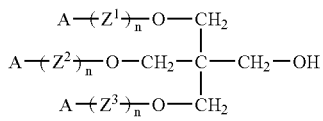

[wherein

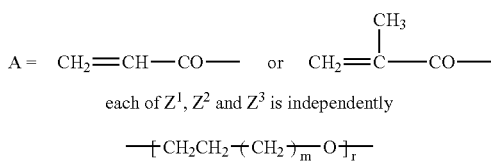

each of $Z^1$, $Z^2$ and $Z^3$ is independently $$-\!\!\!+\!CH_2CH_2\!-\!(\!CH_2\!-\!)_m\!-\!O\!-\!)_r\!-$$

[wherein m is an integer of 0 through 4 and r is an integer of 1 through 20.] n is 0 or 1.]

Chemical Formula 6:

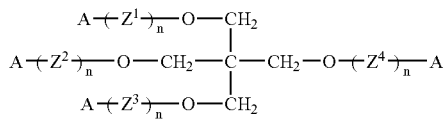

[wherein

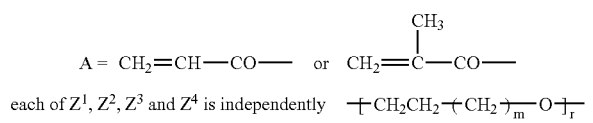

each of $Z^1$, $Z^2$, $Z^3$ and $Z^4$ is independently $-\!+\!CH_2CH_2\!-\!(\!CH_2\!-\!)_m\!O\!-\!)_r\!-$

[wherein m is an integer of 0 through 4 and r is an integer of 1 through 20.] n is 0 or 1.]

Chemical Formula 7:

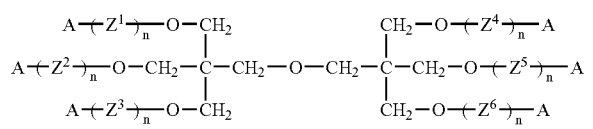

[wherein

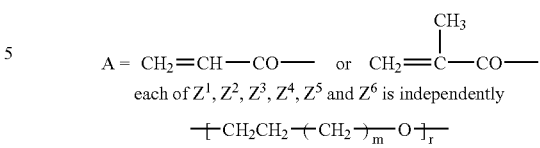

each of $Z^1$, $Z^2$, $Z^3$, $Z^4$, $Z^5$ and $Z^6$ is independently $$-\!\!\!+\!CH_2CH_2\!-\!(\!CH_2\!-\!)_m\!O\!-\!)_r\!-$$

[wherein m is an integer of 0 through 4 and r is an integer of 1 through 20.] n is 0 or 1.]

One of these cross-linkable polymeric monomers (f) may be singly used or a plurality of them may be mixedly used. In the case where the mixing ratio of the cross-linkable polymeric monomer (f) is excessive, the permeation of the hydrophobic acidic group-containing polymeric monomer (a) into a dentine may be lowered so as to lower the adhesive strength, and in the case where the mixing ratio is deficient, the curing property of the composition may be too low to exhibit high adhesive strength. The mixing ratio of the cross-linkable polymeric monomer (f) is preferably 5 through 60 wt %, more preferably 10 through 50 wt % and most preferably 20 through 40 wt % based on the total weight of the dental adhesive composition.

In order to adjust the hydrophilicity/hydrophobicity balance and the viscosity or to improve the mechanical strength or the adhesive strength of the composition, a polymeric monomer apart from the hydrophobic acidic group-containing polymeric monomer (a), the water-soluble polymeric monomer (b) and the cross-linkable polymeric monomer (f) may be included.

Examples of such a polymeric monomer are methyl(meth)acrylate, ethyl(meth)acrylate, isopropyl(meth)acrylate, isobutyl(meth)acrylate, benzyl(meth)acrylate, lauryl(meth)acrylate, 2,3-dibromopropyl(meth)acrylate, 3-methacyloyloxypropyl trimethoxysilane, 11-methacryloyloxyundecyl trimethoxysilane and 10-hydroxydecyl(meth)acrylate.

One of these polymeric monomers may be singly used or a plurality of them may be mixedly used. In the case where the mixing ratio of such a polymeric monomer is excessive, the permeation into a dentine may be lowered so as to lower the adhesive strength. In general, the mixing ratio of such a polymeric monomer is preferably 40 wt % or less, more preferably 20 wt % or less and most preferably 10 wt % or less based on the total weight of the dental adhesive composition.

The basic compound (g) is used in the present invention because the hydrophobic acidic group-containing polymeric monomer (a) is used instead of a water-soluble acidic group-containing polymeric monomer. Specifically, although the hydrophobic acidic group-containing polymeric monomer (a) exhibits higher water resistance after the polymeric curing than a water-soluble acidic group-containing polymeric monomer as described above, it is poor at the permeation into a dentine. Therefore, in order to improve the permeation into a dentine of the hydrophobic acidic group-containing polymeric monomer (a) for improving the adhesive strength in this invention, a part of the hydrophobic acidic group-containing polymeric monomer (a) is allowed to react with the basic compound (g) so as to produce a water-soluble salt. Furthermore, when the basic compound (g) is included, the acidity of the composition is lowered, so as to suppress hydrolysis of the included polymeric monomers, and hence, the storage stability is largely improved. The thus produced salt is dissociated in an aqueous solution to be present separately as an anion and a cation. The basic compound (g) is allowed to react not with the whole of but with a part of the hydrophobic acidic group-containing polymeric monomer (a) because when the whole is reacted to produce the water-soluble salt, the resultant pH is too high to decalcify a dentine, and hence, the permeation is lowered on the contrary.

As the basic compound (g), a compound for producing, through the reaction with the hydrophobic acidic group-containing polymeric monomer (a), a salt that can be dissolved in water in a concentration of 0.016 M (mole/liter) or more at 25° C. is preferably used, a compound for producing a salt that can be dissolved in water in a concentration of 0.16 M or more is more preferably used and a compound for producing a salt that can be dissolved in water in a concentration of 0.32 M or more is most preferably used. Specific examples are hydroxides of alkali metals such as sodium hydroxide, lithium hydroxide and potassium hydroxide; a salt of an alkali metal and a weak acid with pKa of 3 or more (a strong basic acid having no aromatic group) such as sodium carbonate, sodium hydrogencarbonate, potassium carbonate, potassium hydrogencarbonate, lithium carbonate, lithium hydrogencarbonate, sodium formate, sodium benzoate, sodium hydrogen oxalate, sodium acetate, potassium acetate, sodium propionate, sodium borate, sodium dihydrogen phosphite, potassium dihydrogen phosphite, sodium dihydrogen phosphate, potassium dihydrogen phosphate, disodium hydrogen phosphate or dipotassium hydrogen phosphate; and amines. Any amine of primary amines, secondary amines and tertiary amines may be used as far as it can produce, together with the hydrophobic acidic group-containing polymeric monomer (a), a salt that can be dissolved in water. It is noted that the aromatic tertiary amine (e) having an electron-withdrawing group is different from the basic compound (g) in that it does not produce a water-soluble salt through a reaction with the hydrophobic acidic group-containing polymeric monomer (a). Preferably, the amines are selected and the mixing ratio is adjusted in accordance with the kind of the hydrophobic acidic group-containing polymeric monomer (a) to be used. Specific examples of the amines are triethanolamine, diethanolamine, methyl diethanolamine, 2-dimethylaminoethyl (meth)acrylate, 3-dimethylaminopropyl(meth)acrylate, 4-dimethylaminobutyl(meth)acrylate, 6-dimethylaminohexyl(meth)acrylate, 10-dimethylaminodecyl(meth)acrylate, 4-dimethylaminophenetyl alcohol, 4-diethylaminophenetyl alcohol, 4-dipropylaminophenetyl alcohol, N,N-di(2-hydroxyethyl)-p-toluidine, N,N-di(2-hydroxypropyl)-p-toluidine, N,N-dimethyl-p-toluidine, N,N-dipropyl-p-toluidine, N,N-diethyl-p-toluidine, N,N-diethoxyethyl-p-toluidine, N,N-dibutoxyethyl-p-toluidine, N,N-di(polyoxyethylene)oxyethyl-p-toluidine, hexamethylenediamine, a dimethylamine aqueous solution, pentamethylenediamine, diethylamine, ethylenediamine, 2-aminoethanol, triethylamine and 2-dimethylaminoethanol.

With respect to the aforementioned basic compounds, in the case where a basic compound is mixed in a ratio of 0.16 mM in a suspension compound similar to soap water including 0.16 mM of 10-methacryloyloxydecyl dihydrogenphosphate (hereinafter referred to as "MDP"), that is, a bivalent hydrophobic phosphoric group-containing polymeric monomer (a-1), and 1 mL of distilled water, if the turbidity of the suspension compound is reduced, this basic compound is preferred, and if the suspension compound becomes a transparent solution, this basic compound is more preferred.

One of these basic compounds (g) may be singly used or a plurality of them may be mixedly used. The basic compound (g) is included so as to make the liquid (composition) have preferably pH 1.5 through 4.0, more preferably pH 1.8 through 3.5 and most preferably pH 2.0 through 3.0. In the case where the pH of the composition is less than 1.5, namely, in the case where the basic compound (g) is deficiently included, the water-solubility of the hydrophobic acidic group-containing polymeric monomer (a) may be so insufficient that the permeation is lowered. On the other hand, in the case where the pH of the composition exceeds 4.0, namely, in the case where the basic compound (g) is excessively included, the decalcification function may be lowered so as to lower the permeation on the contrary. In the case where the basic compound (g) is included so as to make the solution have pH 4.0 or less, since almost the whole of the included basic compound (g) is allowed to react with a part of the hydrophobic acidic group-containing polymeric monomer (a), the resultant composition includes substantially no basic compound (g) but includes an unreacted part of the hydrophobic acidic group-containing polymeric monomer (a) and a cation and an anion produced through the dissociation of the salt.

Although the water-soluble salt itself produced through the reaction between the basic compound (g) and the acidic group-containing polymeric monomer (a) has a low polymeric curing property, since the cross-linkable polymeric monomer (f) with a high polymeric curing property is separately included, the dental adhesive composition of this invention attains a high polymeric curing property. In the case where the mixing ratio of the cross-linkable polymeric monomer (f) is too large, however, the permeation into a dentine is lowered, and hence, a high adhesive property may not be attained. In other words, the proportion of the cross-linkable polymeric monomer (f) to the acidic group-containing polymeric monomer (a) may largely affect the polymeric curing property and the adhesive property of the composition. The proportion of the cross-linkable polymeric monomer (f) to 100 parts by weight of the basic compound (g) for obtaining a composition good at both the polymeric curing property and the adhesive property is preferably 25 through 60000 parts by weight, more preferably 50 through 12000 parts by weight and most preferably 100 through 6000 parts by weight.

In order to attain a high adhesive property onto a dentine, the salt of the acidic group-containing polymeric monomer (a) and the basic compound (g) that reacts with apatite of the dentine should sufficiently permeate into the dentine. Therefore, the salt corresponding to the reaction product of the acidic group-containing polymeric monomer (a) and the basic compound (g) should be water-soluble. As a preferable combination of them, a combination (i) of a (meth)acrylate-based polymeric monomer including, in one molecule, at least one univalent phosphoric group [a phosphonico group: —P(=O)(OH)—], bivalent phosphoric group [a phosphono group: —P(=O)(OH)$_2$] or pyrophosphoric group [—P(=O)(OH)—O—P(=O)(OH)—] corresponding to the acidic group-containing polymeric monomer (a) and aromatic secondary amine or aromatic tertiary amine corresponding to the basic compound (g) is preferred, a combination (ii) of the aforementioned (meth)acrylate-based polymeric monomer corresponding to the acidic group-containing polymeric monomer (a) and aliphatic secondary amine or aliphatic tertiary amine corresponding to the basic compound (g) is more preferred, and a combination (iii) of the aforementioned (meth)acrylate-based polymeric monomer corresponding to the acidic group-containing polymeric monomer (a) and aliphatic secondary amine having a hydroxyl group or aliphatic tertiary amine having a hydroxyl group corresponding to the basic compound (g) is most preferred.

Examples of the combination (i) are 10-(meth)acryloyloxydecyl dihydrogenphosphate and N,N-bis(2-hydroxyethyl)-p-toluidine; 10-(meth)acryloyloxydecyl dihydrogenphosphate and 4-dimethylaminophenetyl alcohol; 10-(meth)

acryloyloxydecyl dihydrogenphosphate and 4-dimethylaminophenetyl alcohol; 10-(meth)acryloyloxydecyl dihydrogenphosphate and N,N-dipropyl-p-toluidine; bis[6-(meth)acryloyloxyhexyl]hydrogenphosphate and 4-dimethylaminophenetyl alcohol; bis[6-(meth)acryloyloxyhexyl] hydrogenphosphate and 4-diethylaminophenetyl alcohol; bis[6-(meth)acryloyloxyhexyl]hydrogenphosphate and N,N-dipropyl-p-toluidine; bis[9-(meth)acryloyloxynonyl] hydrogenphosphate and N,N-bis(2-hydroxyethyl)-p-toluidine; 1,3-di(meth)acryloyloxypropyl dihydrogenphosphate and 4-dimethylaminophenetyl alcohol; bis(6-methacryloyloxyhexyl)pyrophosphate and N,N-bis(2-hydroxyethyl)-p-toluidine; and bis(8-methacryloyloxyoctyl)pyrophosphate and N,N-bis(2-hydroxyethyl)-p-toluidine.

Examples of the combination (ii) are 10-(meth)acryloyloxydecyl dihydrogenphosphate and triethylamine; 10-(meth)acryloyloxydecyl dihydrogenphosphate and diethylamine; 10-(meth)acryloyloxydecyl dihydrogenphosphate and 2-diethylaminoethyl(meth)acrylate; 10-(meth)acryloyloxydecyl dihydrogenphosphate and 3-dimethylaminopropyl (meth)acrylate; bis[6-(meth)acryloyloxyhexyl]hydrogenphosphate and triethylamine; bis[6-(meth)acryloyloxyhexyl] hydrogenphosphate and diethylamine; bis[6-(meth)acryloyloxyhexyl]hydrogenphosphate and 2-diethylaminoethyl (meth)acrylate; bis[6-(meth)acryloyloxyhexyl] hydrogenphosphate and 3-dimethylaminopropyl(meth) acrylate; bis[10-(meth)acryloyloxydecyl] hydrogenphosphate and triethylamine; 1,3-di(meth) acryloyloxypropyl dihydrogenphosphate and diethylamine; bis(6-methacryloyloxyhexyl)pyrophosphate and triethylamine; and bis(8-methacryloyloxyoctyl)pyrophosphate and triethylamine.

Examples of the combination (iii) are 10-(meth)acryloyloxydecyl dihydrogenphosphate and triethanolamine; 10-(meth)acryloyloxydecyl dihydrogenphosphate and methyl diethanolamine; 8-(meth)acryloyloxyoctyl dihydrogenphosphate and triethanolamine; 6-(meth)acryloyloxyhexyl dihydrogenphosphate and methyl diethanolamine; and 12-(meth) acryloyloxydodecyl dihydrogenphosphate and triethanolamine.

A water-soluble volatile organic solvent (h) may be included in order to improve the adhesive strength, the coating property, the permeation into a dentine and the solubility in the water (c) of the acidic group-containing polymeric monomer (a), the photopolymerization initiator (d) and the cross-linkable polymeric monomer (f). As the water-soluble volatile organic solvent (h), an organic solvent that has a boiling point of 150° C. or less at normal pressure and can be dissolved in water at 25° C. in solubility of 5 wt % or more, more preferably 30 wt % or more and most preferably in an arbitrary ratio is generally used. In particular, a water-soluble volatile organic solvent with a boiling point of 100° C. or less at normal pressure is preferably used. Specific examples are ethanol, methanol, 1-propanol, isopropyl alcohol, acetone, methyl ethyl ketone, 1,2-dimethoxy ethane, 1,2-diethoxy ethane and tetrahydrofuran.

One of these water-soluble volatile organic solvents (h) may be singly used or a plurality of them may be mixedly used. When the mixing ratio of the water-soluble volatile organic solvent (h) is excessive, the adhesive strength may be lowered. The mixing ratio of the water-soluble volatile organic solvent (h) is preferably 1 through 70 wt %, more preferably 5 through 50 wt % and most preferably 10 through 30 wt % based on the total weight of the dental adhesive composition.

A filler (i) may be included in order to improve the adhesive strength, the coating property, the flowability, the X-ray impermeability and the mechanical strength. One kind of filler (i) may be singly used or a plurality of fillers may be mixedly used. As the filler (i), an inorganic filler, an organic filler or a complex filler of an inorganic filler and an organic filler may be used.

Examples of the inorganic filler are silica; a mineral including, as a matrix, silica such as kaoline, clay, isinglass or mica; and ceramics and glass including silica as a matrix and further including $Al_2O_3$, $B_2O_3$, $TiO_2$, $ZrO_2$, $BaO$, $La_2O_3$, $SrO_2$, $CaO$, $P_2O_5$ or the like. As such glass, lanthanum glass, barium glass, strontium glass, soda glass, lithium borosilicate glass, zinc glass, fluoroalumino silicate glass, borosilicate glass or bioglass is suitably used. Furthermore, crystalline quartz, hydroxy-apatite, alumina, titanium oxide, yttrium oxide, zirconia, calcium phosphate, barium sulfate, aluminum hydroxide, sodium fluoride, potassium fluoride, sodium monofluorophosphate, lithium fluoride or ytterbium fluoride is also suitably used.

Examples of the organic filler are polymethyl methacrylate, polyethyl methacrylate, a polymer of polyfunctional methacrylate, polyamide, polystyrene, polyvinyl chloride, chloroprene rubber, nitrile rubber and styrene-butadiene rubber.

Examples of the complex filler of an inorganic filler and an organic filler are organo-mineral complex fillers such as a filler obtained by dispersing an inorganic filler in an organic filler and an inorganic filler coated with any of various polymeric monomers.

In order to improve the curing property, the mechanical strength and the coating property, the filler (i) may be subjected to surface-treating with a known surface-treatment agent such as a silane coupling agent. Examples of the surface-treatment agent used in this case are vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane and γ-aminopropyltriethoxysilane.

As the filler (i), a fine grain filler with a primary particle diameter of 0.001 through 0.1 μm is preferably used from the viewpoint of the adhesive strength and the coating property. Specific examples of such a filler are "Aerosil OX50", "Aerosil 50", "Aerosil 200", "Aerosil 380", "Aerosil R972" and "Aerosil 130" (all of which are manufactured by Nippon Aerosil Co., Ltd.; trade names).

The mixing ratio of the filler (i) is preferably 0.1 through 30 wt %, more preferably 0.5 through 20 wt % and most preferably 1 through 10 wt % based on the total weight of the dental adhesive composition.

In order to provide acid resistance to a dentine, a fluoride releasing material may be included. Examples of the fluoride releasing material are fluorine glass such as fluoroamino silicate glass; a metal fluoride such as sodium fluoride, potassium fluoride, sodium monofluorophosphate, lithium fluoride or ytterbium fluoride; a fluoride releasing polymer such as a copolymer of methyl methacrylate and fluoride methacrylate; and a fluoride releasing material such as cetyl amine hydrofluorate.

A stabilizer (a polymerization inhibitor), a coloring agent, a fluorescent agent or a UV absorber may be included. Also, an antibacterial substance such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride or Triclosan may be included.

Next, an exemplified use of the dental adhesive composition of the present invention will be described. First, the dental adhesive composition of the invention is applied on a teeth to be treated with a sponge or a brush, and is allowed to stand for 0 second (namely, air blowing described below is immediately performed) through 120 seconds, preferably 1 through 60 seconds, more preferably 5 through 30 seconds and most preferably 10 through 20 seconds, or is rubbed on the surface of the dentine with a sponge or the like for 60 seconds or less. Subsequently, the air blowing is performed with a dental air syringe, and thereafter, a filling repairing material such as a composite resin, cement or a pit and fissure sealant is applied on the surface coated with the dental adhesive composition, so as to cure them simultaneously. Since the dental adhesive composition of the invention includes the photopolymerization initiator (d), the dental adhesive composition applied on the surface of the dentine is preferably polymerically cured by irradiating with a dental visible light irradiator or the like before applying the filling repairing material because higher adhesive strength can be thus attained. According to the dental adhesive composition of the invention, there is no need to perform preprocessing using a phosphoric acid etching agent or a self-etching primer, and mixing is not necessary because it is one-part type.

The dental adhesive composition of the present invention exhibits high adhesive strength not only on a dentine but also on a crown repairing material (a metal, a porcelain, ceramics, a composite cured substance or the like) broken in a mouth cavity. In the case where the dental adhesive composition of the invention is used for adhering a crown repairing material, the dental adhesive composition of the invention may be used in combination with a primer such as a commercially available metal adhering primer or porcelain adhering primer, or a tooth plane cleaning agent such as hypochlorite or hydrogen peroxide.

Embodiments

The present invention will now be described in detail on the basis of preferred embodiments thereof, and it is noted that the invention is not limited to the following embodiments. Abbreviations used in description below stand for the following:

[Acidic Group—Containing Polymeric Monomer]
MDP: 10-methacryloyloxydecyl dihydrogenphosphate
Bis-MHP: bis[6-(meth)acryloyloxyhexyl]hydrogenphosphate
POP: bis(8-methacryloyloxyoctyl)pyrophosphate
4-MDT: 4-methacryloyloxydecyloxycarbonylphthalic acid
MA: maleic acid

[Water-soluble polymeric monomer (b)]
HEMA: 2-hydroxyethyl methacrylate
9G: nonaethylene glycol dimethacrylate

[Photopolymerization initiator (d)]
CQ: dl-camphorquinone
TMDPO: 2,4,6-trimethylbenzoyldiphenylphosphine oxide

[Aromatic Tertiary Amine (e) Having an Electron-withdrawing Group]
DABB: n-butoxyethyl 4-N,N-dimethylaminobenzoate
DABE: ethyl 4-N,N-dimethylaminobenzoate
DMAI: isoamyl 4-dimethylaminobenzoate
DMAB: 4-N,N-dimethylaminobenzophenone

[Cross-linkable polymeric monomer (f)]
Bis-GMA: bisphenol A diglycidyl methacrylate
UDMA: [2,2,4-trimethylhexamethylene bis(2-carbamoyloxyethyl)]dimethacrylate
Bis4: a cross-linkable polymeric monomer (f) represented by the following Chemical Formula 8:

Chemical Formula 8:

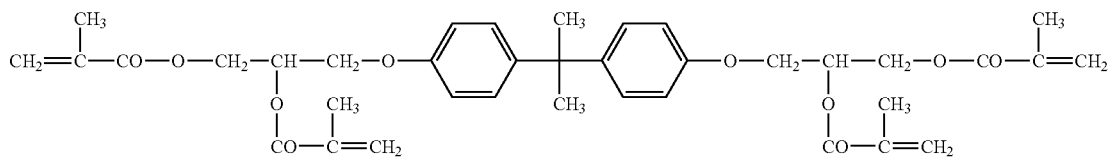

Bis-M3: a cross-linkable polymeric monomer (f) represented by the following Chemical Formula 9:

Chemical Formula 9:

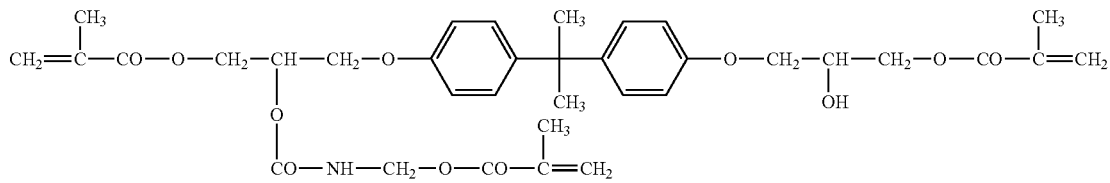

Bis-M4: a cross-linkable polymeric monomer (f) represented by the following Chemical Formula 10:

Chemical Formula 10:

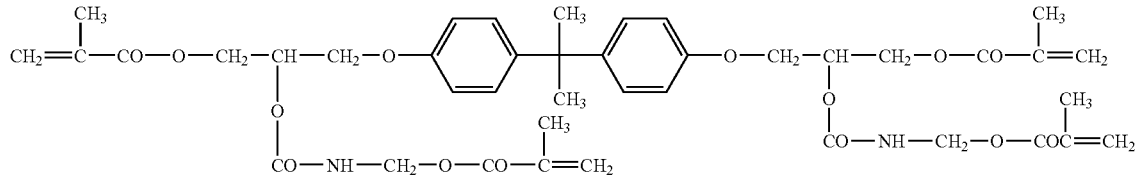

U₄TH: a cross-linkable polymeric monomer (f) represented by the following Chemical Formula 11:

Chemical Formula 11:

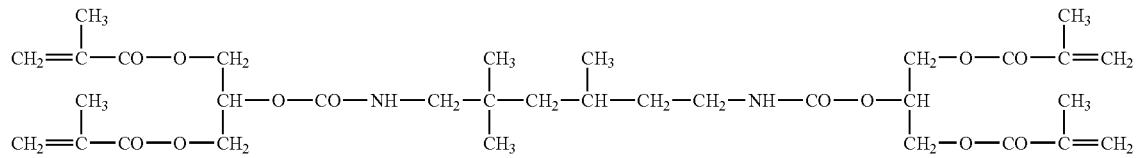

[Basic Compound]
  NaOH: sodium hydroxide
  Ca(OH)$_2$: potassium hydroxide
  NaHCO$_3$: sodium hydrogencarbonate
  K$_2$CO$_3$: potassium carbonate
  CH$_3$COONa: sodium acetate
  BSS: sodium benzenesulfinate
  TPSS: sodium 2,4,6-triisopropylbenzenesulfinate
  TEA: triethanolamine
  MDA: methyl diethanolamine
  DMAEMA: 2-dimethylaminoethyl methacrylate
  DEPT: N,N-bis(2-hydroxyethyl)-p-toluidine
  DAPA: 4-dimethylaminophenetyl alcohol
  DEPA: 4-diethylaminophenetyl alcohol
  ED: ethylenediamine
  AE: 2-aminoethanol
  TE: triethylamine

[Filler (i)]
  R972: fine grain silica manufactured by Aerosil

[Other]
  BHT: 2,6-di-t-butyl-4-methylphenol (stabilizer (polymerization inhibitor))

Embodiment 1

A dental adhesive composition was prepared by mixing MDP (15 parts by weight), NaOH (5 parts by weight), HEMA (35 parts by weight), distilled water (10 parts by weight), Bis-GMA (35 parts by weight), TMDPO (2 parts by weight), CQ (1 part by weight), DABB (1 part by weight) and BHT (0.05 part by weight).

Embodiments 2 through 35

Thirty four kinds of dental adhesive compositions were prepared in the same manner as in Embodiment 1 except that the kinds of the hydrophobic acidic group-containing polymeric monomer (a) and/or the basic compound (g) were different and the mixing ratios of the cross-linkable polymeric monomer (f) and the basic compound (g) were different.

COMPARATIVE EXAMPLE 1

A dental adhesive composition was prepared in the same manner as in Embodiment 1 except that NaOH was not included.

COMPARATIVE EXAMPLES 2 through 7

Six kinds of dental adhesive compositions were prepared in the same manner as in Embodiment 1 except that NaOH (5 parts by weight) was replaced with Ca(OH)$_2$, BSS, TPSS, DABE, DMAI or DMAB (5 parts by weight).

COMPARATIVE EXAMPLE 8

A dental adhesive composition was prepared in the same manner as in Embodiment 1 except that MDP (15 parts by weight) was replaced with MA (15 parts by weight).

The adhesive strength and the storage stability of the dental adhesive compositions prepared in Embodiments 1 through 35 and Comparative Examples 1 through 8 were examined by an adhesive strength testing method and a storage stability testing method described below. The results are listed in Tables 1 and 2 below. Each numerical value of adhesive strength listed in Tables 1 and 2 is an average of measured values obtained in eight test pieces. Each photopolymerization time listed in Tables 1 and 2 was measured by a photopolymerization time measuring method described below. Each value of the photopolymerization time listed in Tables 1 and 2 is an average of five measured values. The solubility in water of the acidic group-containing polymeric monomer and the solubility in water of a reaction product (a salt) of the acidic group-containing polymeric monomer and the basic compound listed in Table 1 were respectively measured by solubility testing methods A and B described below. The adhesive strength, the storage stability and the solubility in water of the acidic group-containing polymeric monomer and its salt obtained in dental adhesive compositions prepared in embodiments and comparative examples described later were examined also by the following testing methods:

[Adhesive Strength Testing Method]

An anterior teeth of a bovine is wet polished to be smooth with #1000 silicon carbide paper (manufactured by Nihon Kenshi Co., Ltd.) so as to expose an enamel surface or a dentine surface, and then, water remaining on the surface is blown off with a dental air syringe. An adhesive tape with a thickness of approximately 150 μm having a hole with a diameter of 3 mm is adhered onto the exposed enamel or dentine surface, a dental adhesive composition (non-stored one) is applied within the hole with a brush and allowed to stand for 20 seconds, and thereafter, the dental adhesive composition is dried with a dental air syringe until its flowability is lost. Subsequently, the dental adhesive composition is irradiated with a dental irradiator (manufactured by Morita Corportion; trade name "JETLITE 3000") for 10 seconds. Then, a photopolymerizable composite resin (manufactured by Kuraray Co., Ltd., trade name "Clearfil AP-X") is placed on the dental adhesive composition and the resultant is covered with a mold releasing film (manufactured by Kuraray Co., Ltd., trade name "Eval"). Thereafter, slide glass is placed on and pressed against the mold releasing film and is cured by irradiating with a dental irradiator "JETLITE 3000" for 20 seconds. Then, one end face (with a circular cross-section) of a stainless steel cylindrical bar with a diameter of 5 mm and a length of 1.5 cm is adhered to this cured surface by using a dental resin cement (manufactured by Kuraray Co., Ltd., trade name "Panavia 21"), and the resultant is allowed to stand for 30 minutes to obtain a test piece. The number of test pieces thus prepared is 16 in total (i.e., 8 test pieces obtained with the enamel surface exposed and 8 test pieces obtained with the dentine surface exposed). Each of the thus obtained test pieces is immersed in distilled water in a sample vessel and is allowed to stand in an incubator set to 37° C. for 24 hours. Then, the test piece is taken out for measuring the adhesive strength. The adhesive strength (tensile adhesive strength) is measured by using a universal testing machine (manufactured by Instron Corporation) with a cross head speed set to 2 mm/min.

[Storage Stability Testing Method]

A dental adhesive composition is placed in a polypropylene vessel and is stored in an incubator set to 50° C. for 3 weeks. Then, the adhesive strength of the dental adhesive composition (stored one) is measured by the aforementioned adhesive strength testing method.

[Photopolymerization Time Measuring Method]

A dental adhesive composition is placed in a glass vessel and is concentrated by drying it with a dental air syringe until it loses a weight corresponding to the content of water and ethanol. Then, 0.015 g of the thus obtained concentrated liquid is dropped onto a washer with a 4 mm hole adhered onto a glass preparation. A thermocouple (manufactured by Okazaki Manufacturing Company, trade code "SKC/C") connected to a recorder (manufactured by Yokogawa Electric Corportion, trade code "Type 3066") is immersed in the concentrated liquid on the washer, and the concentrated liquid is irradiated with a dental irradiator "JETLITE 3000" from below the preparation. Time elapsed from the start of the irradiation until exothermic top is caused through curing is obtained as the photopolymerization time (sec.).

[Solubility Testing Method A for Solubility in Water of Acidic Group-Containing polymeric monomer]

Distilled water (0.9 g) and an acidic group-containing polymeric monomer (0.1 g) are put in a transparent vessel of 10 mL in an environment of 25° C., the resultant liquid is stirred with a stirrer bar and the turbidity of the liquid is visually observed. When the liquid is clear, it is determined that the acidic group-containing polymeric monomer has solubility of 10 wt % or more, and it is evaluated as ×. When the liquid is not clear, 1 g of distilled water is further added to the liquid, the resultant liquid is stirred with a stirrer bar and the turbidity of the liquid is visually observed again. When the liquid becomes clear, it is determined that the acidic group-containing polymeric monomer has solubility of 5 through 10 wt %, and it is evaluated as Δ, and when the liquid does not become clear, it is determined that the acidic group-containing polymeric monomer has solubility less than 5 wt %, and it is evaluated as o.

[Solubility Testing Method B for Solubility in Water of Salt of Acidic Group-Containing polymeric monomer]

Distilled water (1 mL) and an acidic group-containing polymeric monomer (16 mM) are put in a transparent vessel of 10 mL in an environment of 25° C., and the resultant liquid is stirred with a stirrer bar so as to prepare a suspension similar to soap water. A basic compound (0.16 mM) is added to the suspension, and change of the turbidity of the suspension is visually observed. When the suspension is changed into a clear liquid, it is determined that the slat of the acidic group-containing polymeric monomer has solubility of 0.16 M or more, and it is evaluated as o. When the turbidity of the suspension is not changed or increased, 9 mL of distilled water is further added to the suspension, the resultant suspension is stirred at room temperature for one day, and the change of the turbidity is visually observed again. When the suspension is changed into a clear liquid, it is determined that the salt of the acidic group-containing polymeric monomer has solubility of 0.016 through 0.16 M, and it is evaluated as Δ, and when the suspension is not changed into a clear liquid, it is determined that the salt of the acidic group-containing polymeric monomer has solubility less than 0.016 M, and it is evaluated as ×.

TABLE 1

| | Acidic group-containing polymeric monomer | Basic compound | Solubility of acidic group-containing polymeric monomer | Solubility of salt | Cross-linkable polymeric monomer (parts by weight) | Basic compound (parts by weight) | Adhesive strength test (MPa) | | Storage stability test (MPa) | | Photo-polymerization time (sec.) |
|---|---|---|---|---|---|---|---|---|---|---|---|
| | | | | | | | Bovine teeth enamel | Bovine teeth dentine | Bovine teeth enamel | Bovine teeth dentine | |
| Emb. 1 | MDP | NaOH | ○ | ○ | 35 | 5 | 15.3 | 14.8 | 14.4 | 13.7 | 8.4 |
| Emb. 2 | MDP | NaOH | ○ | ○ | 39.5 | 0.5 | 14.7 | 13.9 | 14.1 | 13.4 | 7.2 |
| Emb. 3 | MDP | NaOH | ○ | ○ | 39.7 | 0.3 | 14.3 | 13.7 | 13.8 | 13.0 | 7.0 |
| Emb. 4 | MDP | LiHCO$_3$ | ○ | ○ | 35 | 5 | 15.2 | 14.7 | 14.5 | 13.6 | 8.1 |

TABLE 1-continued

| | Acidic group-containing polymeric monomer | Basic compound | Solubility of acidic group-containing polymeric monomer | Solubility of salt | Cross-linkable polymeric monomer (parts by weight) | Basic compound (parts by weight) | Adhesive strength test (MPa) Bovine teeth enamel | Adhesive strength test (MPa) Bovine teeth dentine | Storage stability test (MPa) Bovine teeth enamel | Storage stability test (MPa) Bovine teeth dentine | Photo-polymerization time (sec.) |
|---|---|---|---|---|---|---|---|---|---|---|---|
| Emb. 5 | MDP | K₂CO₃ | ○ | ○ | 35 | 5 | 15.6 | 14.6 | 14.7 | 13.8 | 8.2 |
| Emb. 6 | MDP | CH₂CO₂Na | ○ | ○ | 35 | 5 | 15.0 | 14.0 | 14.5 | 13.0 | 8.5 |
| Emb. 7 | MDP | TEA | ○ | ○ | 35 | 5 | 15.3 | 14.7 | 14.6 | 13.6 | 5.1 |
| Emb. 8 | MDP | TEA | ○ | ○ | 25 | 15 | 14.9 | 14.4 | 14.3 | 13.4 | 5.8 |
| Emb. 9 | MDP | TEA | ○ | ○ | 20 | 20 | 14.6 | 14.2 | 14.2 | 13.3 | 6.0 |
| Emb. 10 | MDP | TEA | ○ | ○ | 39.5 | 0.5 | 14.8 | 14.4 | 14.4 | 13.3 | 4.7 |
| Emb. 11 | MDP | TEA | ○ | ○ | 39.7 | 0.3 | 14.6 | 14.1 | 14.2 | 13.1 | 4.6 |
| Emb. 12 | MDP | MDA | ○ | ○ | 35 | 5 | 15.6 | 14.6 | 14.8 | 13.5 | 5.3 |
| Emb. 13 | MDP | ED | ○ | ○ | 35 | 5 | 15.4 | 14.6 | 14.9 | 13.4 | 6.9 |
| Emb. 14 | MDP | AE | ○ | ○ | 35 | 5 | 15.1 | 14.7 | 14.4 | 13.6 | 6.5 |
| Emb. 15 | MDP | TE | ○ | ○ | 35 | 5 | 15.0 | 14.9 | 14.6 | 13.8 | 6.2 |
| Emb. 16 | MDP | TE | ○ | ○ | 39.5 | 0.5 | 14.7 | 14.6 | 14.5 | 13.5 | 5.8 |
| Emb. 17 | MDP | TE | ○ | ○ | 20 | 20 | 14.6 | 14.6 | 14.4 | 13.4 | 6.8 |
| Emb. 18 | MDP | DMAEMA | ○ | ○ | 35 | 5 | 15.4 | 14.8 | 14.5 | 13.5 | 6.8 |
| Emb. 19 | MDP | DEPT | ○ | ○ | 35 | 5 | 15.5 | 14.8 | 14.7 | 13.3 | 7.2 |
| Emb. 20 | MDP | DEPT | ○ | ○ | 39.7 | 0.3 | 15.1 | 14.3 | 14.1 | 12.8 | 6.6 |
| Emb. 21 | MDP | DEPT | ○ | ○ | 20 | 20 | 15.0 | 14.3 | 14.0 | 12.9 | 7.8 |
| Emb. 22 | MDP | DAPA | ○ | ○ | 35 | 5 | 15.5 | 14.9 | 14.6 | 13.7 | 7.5 |
| Emb. 23 | MDP | DEPA | ○ | ○ | 35 | 5 | 15.3 | 14.7 | 14.4 | 13.8 | 7.3 |
| Emb. 24 | Bis-MHP | NaOH | ○ | ○ | 35 | 5 | 14.4 | 14.1 | 13.4 | 12.8 | 8.0 |
| Emb. 25 | Bis-MHP | TE | ○ | ○ | 35 | 5 | 14.6 | 14.2 | 13.7 | 13.0 | 6.9 |
| Emb. 26 | Bis-MHP | TE | ○ | ○ | 39.5 | 0.5 | 14.3 | 13.9 | 13.6 | 12.9 | 6.2 |
| Emb. 27 | Bis-MHP | TE | ○ | ○ | 20 | 20 | 14.1 | 13.8 | 13.3 | 12.8 | 7.8 |
| Emb. 28 | Bis-MHP | DEPT | ○ | ○ | 35 | 5 | 14.5 | 14.0 | 13.4 | 12.9 | 7.1 |
| Emb. 29 | Bis-MHP | TEA | ○ | ○ | 35 | 5 | 14.8 | 14.2 | 13.9 | 13.1 | 6.5 |
| Emb. 30 | POP | NaOH | ○ | ○ | 35 | 5 | 14.0 | 13.5 | 13.3 | 12.2 | 8.1 |
| Emb. 31 | POP | K₂CO₃ | ○ | ○ | 35 | 5 | 14.1 | 13.7 | 13.4 | 12.3 | 8.3 |
| Emb. 32 | POP | TEA | ○ | ○ | 35 | 5 | 14.2 | 13.7 | 13.5 | 12.0 | 7.1 |
| Emb. 33 | 4-MDT | NaOH | ○ | ○ | 35 | 5 | 13.5 | 12.0 | 12.1 | 11.3 | 8.7 |
| Emb. 34 | 4-MDT | K₂CO₃ | ○ | ○ | 35 | 5 | 13.2 | 12.1 | 12.0 | 11.0 | 8.8 |
| Emb. 35 | 4-MDT | TEA | ○ | ○ | 35 | 5 | 13.4 | 12.0 | 12.4 | 11.2 | 8.3 |

TABLE 2

| | Acidic group-containing polymeric monomer | Basic compound | Solubility of acidic group-containing polymeric monomer | Solubility of salt | Cross-linkable polymeric monomer (parts by weight) | Basic compound (parts by weight) | Adhesive strength test (MPa) Bovine teeth enamel | Adhesive strength test (MPa) Bovine teeth dentine | Storage stability test (MPa) Bovine teeth enamel | Storage stability test (MPa) Bovine teeth dentine | Photo-polymerization time (sec.) |
|---|---|---|---|---|---|---|---|---|---|---|---|
| CE. 1 | MDP | None | ○ | — | 35 | 5 | 11.0 | 9.9 | 8.4 | 5.6 | 7.6 |
| CE. 2 | MDP | Ca(OH)₂ | ○ | X | 35 | 5 | 7.4 | 5.5 | 4.5 | 3.2 | unmeasurable |
| CE. 3 | MDP | BSS | ○ | X | 35 | 5 | 8.7 | 5.6 | 6.5 | 3.1 | unmeasurable |
| CE. 4 | MDP | TPSS | ○ | X | 35 | 5 | 8.6 | 5.8 | 6.5 | 3.4 | unmeasurable |
| CE. 5 | MDP | DABE | ○ | X | 35 | 5 | 9.9 | 6.8 | 7.7 | 4.3 | 7.7 |
| CE. 6 | MDP | DMAI | ○ | X | 35 | 5 | 9.7 | 6.7 | 7.5 | 4.2 | 7.8 |
| CE. 7 | MDP | DMAB | ○ | X | 35 | 5 | 9.8 | 6.7 | 7.6 | 3.1 | 7.5 |
| CE. 8 | MA | NaOH | X | ○ | 35 | 5 | 3.2 | 3.0 | 1.0 | 1.1 | 13.1 |

As shown in Table 1, all the dental adhesive compositions of Embodiments 1 through 35 are good both at the adhesive strength of non-stored ones and at the adhesive strength of stored ones. This reveals that the dental adhesive composition of the present invention exhibits high adhesive strength on both enamel and dentine and has high storage stability. On the other hand, as shown in Table 2, the dental adhesive composition of Comparative Example 1 not including a basic compound is poor both at the adhesive strength of non-stored one and at the adhesive strength of stored one. The adhesive strength of non-stored one of the dental adhesive composition of Comparative Example 1 is low because the permeation of the hydrophobic acidic group-containing polymeric monomer (MDP) into a dentine is poor, and the adhesive strength of stored one is low because the pH of the composition is so low that a part of the polymeric monomers is hydrolyzed during the storage. In the dental adhesive compositions of Comparative Examples 2 through 7 each including the basic compound for producing a salt through a reaction with the hydrophobic acidic group-containing polymeric monomer (MDP), the adhesive strength of non-stored ones and the adhesive strength of stored ones are low because the produced salt is water-insoluble and hence the permeation into a dentine is poor. In the dental adhesive composition of Comparative Example 8 including the water-soluble acidic group-containing polymeric monomer (MA), both the adhesive strength of non-stored one and the adhesive strength of stored one are very low because the water resistance of the cured substance is very low.

Embodiment 36

A dental adhesive composition was prepared by mixing MDP (12 parts by weight), NaOH (3 parts by weight), HEMA (30 parts by weight), distilled water (15 parts by weight), Bis-GMA (30 parts by weight), ethanol (10 parts by weight), TMDPO (2 parts by weight), CQ (1 part by weight), DABB (1 part by weight) and BHT (0.05 part by weight).

Embodiments 37 through 54

Eighteen kinds of dental adhesive compositions were prepared in the same manner as in Embodiment 36 except that the kinds of the hydrophobic acidic group-containing polymeric monomer (a) and/or the basic compound (g) were different.

The adhesive strength and the storage stability of the dental adhesive compositions prepared in Embodiments 36 through 54 were examined. The test results are listed in Table 3.

TABLE 3

| | Acidic group-containing polymeric monomer | Basic compound | Solubility of acidic group-containing polymeric monomer | Solubility of salt | Adhesive strength test (MPa) | | Storage stability test (MPa) | | Photo-polymerization time (sec.) |
|---|---|---|---|---|---|---|---|---|---|
| | | | | | Bovine teeth enamel | Bovine teeth dentine | Bovine teeth enamel | Bovine teeth dentine | |
| Emb. 36 | MDP | NaOH | ○ | ○ | 16.1 | 15.4 | 15.4 | 14.5 | 8.3 |
| Emb. 37 | MDP | LiHCO$_3$ | ○ | ○ | 16.2 | 15.4 | 15.5 | 14.3 | 8.0 |
| Emb. 38 | MDP | K$_2$CO$_3$ | ○ | ○ | 16.3 | 15.3 | 15.7 | 14.6 | 8.0 |
| Emb. 39 | MDP | CH$_3$CO$_2$Na | ○ | ○ | 16.3 | 15.2 | 15.8 | 14.2 | 8.3 |
| Emb. 40 | MDP | TEA | ○ | ○ | 16.5 | 15.5 | 15.6 | 14.6 | 5.0 |
| Emb. 41 | MDP | MDA | ○ | ○ | 16.7 | 15.1 | 15.6 | 14.7 | 5.2 |
| Emb. 42 | MDP | ED | ○ | ○ | 16.8 | 15.3 | 15.4 | 14.1 | 6.7 |
| Emb. 43 | MDP | AE | ○ | ○ | 16.2 | 15.6 | 15.3 | 14.3 | 6.3 |
| Emb. 44 | MDP | TE | ○ | ○ | 16.3 | 15.7 | 15.2 | 14.5 | 6.0 |
| Emb. 45 | MDP | DMAEMA | ○ | ○ | 16.7 | 15.5 | 15.5 | 14.8 | 6.5 |
| Emb. 46 | MDP | DEPT | ○ | ○ | 16.5 | 15.3 | 15.3 | 14.4 | 7.0 |
| Emb. 47 | MDP | DAPA | ○ | ○ | 16.5 | 15.2 | 15.6 | 14.2 | 7.4 |
| Emb. 48 | MDP | DEPA | ○ | ○ | 16.3 | 15.1 | 15.6 | 14.1 | 7.1 |
| Emb. 49 | POP | NaOH | ○ | ○ | 15.1 | 14.3 | 14.7 | 13.7 | 8.0 |
| Emb. 50 | POP | K$_2$CO$_3$ | ○ | ○ | 15.2 | 14.2 | 14.8 | 13.2 | 8.2 |
| Emb. 51 | POP | TEA | ○ | ○ | 15.0 | 14.0 | 14.4 | 13.5 | 7.0 |
| Emb. 52 | 4-MDT | NaOH | ○ | ○ | 14.3 | 13.1 | 13.6 | 12.5 | 8.5 |
| Emb. 53 | 4-MDT | K$_2$CO$_3$ | ○ | ○ | 14.1 | 13.2 | 13.4 | 12.6 | 8.7 |
| Emb. 54 | 4-MDT | TEA | ○ | ○ | 14.2 | 13.4 | 13.5 | 12.3 | 8.1 |

It is understood from Table 3 and Table 1 above that the adhesive strength and the storage stability are further improved by adding ethanol (a water-soluble volatile organic solvent (h)) to the dental adhesive composition of this invention.

Embodiments 55

A dental adhesive composition was prepared by mixing MDP (12 parts by weight), NaOH (3 parts by weight), HEMA (25 parts by weight), distilled water (15 parts by weight), Bis-GMA (25 parts by weight), ethanol (20 parts by weight), TMDPO (2 parts by weight), CQ (1 part by weight), DABB (1 part by weight), BHT (0.05 part by weight) and R972 (7 parts by weight).

Embodiments 56 through 73

Eighteen kinds of dental adhesive compositions were prepared in the same manner as in Embodiment 55 except that the kinds of the hydrophobic acidic group-containing polymeric monomer (a) and/or the basic compound (g) were different.

The adhesive strength and the storage stability of the dental adhesive compositions prepared in Embodiments 55 through 73 were examined. The test results are listed in Table 4.

It is understood from Table 4 and Table 3 above that the adhesive strength and the storage stability are further improved by adding R972 (a filler (i)) to the dental adhesive composition of the invention.

Embodiments 74 through 83

Ten kinds of dental adhesive compositions were prepared by mixing a hydrophobic acidic group-containing polymeric monomer, that is, MDP (15 parts by weight), DAPA or NaOH (5 parts by weight), HEMA or 9G (25 parts by weight), distilled water (15 parts by weight), Bis-GMA, UDMA, U4TH, Bis4, Bis-M4 or Bis-M3 (25 parts by weight), acetone (15 parts by weight), TMDPO (2 parts by weight), CQ (1 part by weight), DABB (1 part by weight), BHT (0.05 part by weight) and R972 (7 parts by weight).

The adhesive strength and the storage stability of the dental adhesive compositions prepared in Embodiments 74 through 83 were examined. The test results are listed in Table 5.

TABLE 4

| | Acidic group-containing polymeric monomer | Basic compound | Solubility of acidic group-containing polymeric monomer | Solubility of salt | Adhesive strength test (MPa) Bovine teeth enamel | Adhesive strength test (MPa) Bovine teeth dentine | Storage stability test (MPa) Bovine teeth enamel | Storage stability test (MPa) Bovine teeth dentine | Photo-polymerization time (sec.) |
|---|---|---|---|---|---|---|---|---|---|
| Emb. 55 | MDP | NaOH | ○ | ○ | 17.7 | 16.7 | 16.4 | 15.3 | 8.2 |
| Emb. 56 | MDP | LiHCO$_3$ | ○ | ○ | 17.6 | 16.6 | 16.8 | 15.4 | 8.0 |
| Emb. 57 | MDP | K$_2$CO$_3$ | ○ | ○ | 17.8 | 16.7 | 16.7 | 15.3 | 8.0 |
| Emb. 58 | MDP | CH$_3$CO$_2$Na | ○ | ○ | 17.4 | 16.8 | 16.9 | 15.6 | 8.1 |
| Emb. 59 | MDP | TEA | ○ | ○ | 17.1 | 16.5 | 16.4 | 15.8 | 5.0 |
| Emb. 60 | MDP | MDA | ○ | ○ | 17.4 | 16.4 | 16.3 | 15.9 | 5.1 |
| Emb. 61 | MDP | ED | ○ | ○ | 17.5 | 16.3 | 16.5 | 15.3 | 6.5 |
| Emb. 62 | MDP | AE | ○ | ○ | 17.8 | 16.8 | 16.8 | 15.3 | 6.1 |
| Emb. 63 | MDP | TE | ○ | ○ | 17.7 | 16.9 | 16.9 | 15.4 | 6.0 |
| Emb. 64 | MDP | DMAEMA | ○ | ○ | 17.5 | 16.6 | 16.5 | 15.7 | 6.5 |
| Emb. 65 | MDP | DEPT | ○ | ○ | 17.3 | 16.5 | 16.3 | 15.6 | 6.9 |
| Emb. 66 | MDP | DAPA | ○ | ○ | 17.2 | 16.6 | 16.9 | 15.5 | 7.3 |
| Emb. 67 | MDP | DEPA | ○ | ○ | 17.4 | 16.8 | 16.1 | 15.4 | 7.1 |
| Emb. 68 | POP | NaOH | ○ | ○ | 17.7 | 16.9 | 16.4 | 15.8 | 7.9 |
| Emb. 69 | POP | K$_2$CO$_3$ | ○ | ○ | 17.6 | 16.5 | 16.6 | 15.9 | 8.1 |
| Emb. 70 | POP | TEA | ○ | ○ | 17.5 | 16.3 | 16.7 | 15.5 | 6.9 |
| Emb. 71 | 4-MDT | NaOH | ○ | ○ | 17.2 | 16.2 | 16.8 | 15.4 | 8.4 |
| Emb. 72 | 4-MDT | K$_2$CO$_3$ | ○ | ○ | 17.8 | 16.1 | 16.5 | 15.5 | 8.5 |
| Emb. 73 | 4-MDT | TEA | ○ | ○ | 17.5 | 16.6 | 16.9 | 15.7 | 8.0 |

TABLE 5

| | Acidic group-containing polymeric monomer (a) | Basic compound (g) | Water-soluble polymeric monomer (b) | Cross-linkable polymeric monomer (f) | Adhesive strength test (MPa) | | Storage stability test (MPa) | |
|---|---|---|---|---|---|---|---|---|
| | | | | | Bovine teeth enamel | Bovine teeth dentine | Bovine teeth enamel | Bovine teeth dentine |
| Emb. 74 | MDP | DAPA | HEMA | Bis-GMA | 17.8 | 16.7 | 16.8 | 15.8 |
| Emb. 75 | MDP | DAPA | HEMA | UDMA | 15.2 | 14.3 | 14.6 | 13.2 |
| Emb. 76 | MDP | DAPA | HEMA | U4TH | 16.7 | 15.9 | 16.5 | 15.2 |
| Emb. 77 | MDP | DAPA | HEMA | Bis4 | 18.8 | 17.5 | 18.5 | 16.6 |
| Emb. 78 | MDP | DAPA | HEMA | Bis-M4 | 18.5 | 17.8 | 18.3 | 16.7 |
| Emb. 79 | MDP | DAPA | HEMA | Bis-M3 | 17.1 | 16.0 | 16.5 | 15.3 |
| Emb. 80 | MDP | NaOH | HEMA | Bis-GMA | 17.5 | 16.8 | 16.8 | 15.7 |
| Emb. 81 | MDP | NaOH | 9G | Bis-GMA | 17.2 | 16.7 | 16.9 | 15.5 |
| Emb. 82 | MDP | NaOH | HEMA | Bis-M4 | 18.5 | 18.0 | 17.7 | 17.5 |
| Emb. 83 | MDP | NaOH | 9G | Bis-M4 | 18.8 | 18.1 | 17.0 | 17.4 |

It is understood from Table 5 that all the dental adhesive compositions of Embodiments 74 through 83 have high adhesive strength and high storage stability.

COMPARATIVE EXAMPLES 9 through 12

Four kinds of dental adhesive compositions were prepared in the same manner as in Embodiment 1 except that one of MDP, HEMA, distilled water and Bis-GMA was not included.

COMPARATIVE EXAMPLE 13

A dental adhesive composition was prepared by mixing MDP (3 parts by weight), 4-methacryloyloxyethyl trimellitic acid (4-MET) (24 parts by weight), 2-hydroxy-1,3-dimethacryloyloxypropane (GDMA) (24 parts by weight), triethylene glycol dimethacrylate (TEGDMA) (5 parts by weight), UDMA (10 parts by weight), distilled water (34 parts by weight), CQ (0.5 part by weight), TMDPO (2 parts by weight) and Aerosil 50 (manufactured by Nippon Aerosil, brand name) (A50) (3 parts by weight). This dental adhesive composition corresponds to a dental adhesive composition described in Embodiment 13 of Japanese Laid-Open Patent Publication No. 2003-73218 (i.e., Patent Document 4 described in Background Art).

COMPARATIVE EXAMPLE 14

A dental adhesive composition was prepared by mixing MDP (15 parts by weight), distilled water (85 parts by weight) and DAPA (7.7 parts by weight). This dental adhesive composition corresponds to a dental adhesive composition described in Embodiment 2 of Japanese Laid-Open Patent Publication No. 2001-49199 (i.e., Patent Document 3 described in Background Art).

The adhesive strength and the storage stability of the dental adhesive compositions prepared in Comparative Examples 9 through 14 were examined. The test results are listed in Table 6.

TABLE 6

| | | Mixing ratio (parts by weight) | | | | | |
|---|---|---|---|---|---|---|---|
| | | Com. Ex. 9 | Com. Ex. 10 | Com. Ex. 11 | Com. Ex. 12 | Com. Ex. 13 | Com. Ex. 14 |
| Dental adhesive composition | MDP | — | 15 | 15 | 15 | Described in Specification | Described in Specification |
| | HEMA | 35 | — | 35 | 35 | | |
| | Distilled water | 10 | 10 | — | 10 | | |
| | Bis-GMA | 35 | 35 | 35 | — | | |
| | TMDPO | 2 | 2 | 2 | 2 | | |
| | CQ | 1 | 1 | 1 | 1 | | |
| | DABB | 1 | 1 | 1 | 1 | | |
| | NaOH | 5 | 5 | 5 | 5 | | |
| | BHT | 0.05 | 0.05 | 0.05 | 0.05 | | |
| Solubility of acidic group-containing polymeric monomer | | ○ | ○ | ○ | ○ | ○ | ○ |
| Solubility of salt | | — | ○ | ○ | ○ | ○ | ○ |
| Adhesive strength test (MPa) | Bovine teeth enamel | 0.0 | 3.0 | 4.0 | 11.5 | 9.0 | 12.0 |
| | Bovine teeth dentine | 0.0 | 1.4 | 3.3 | 4.4 | 8.9 | 10.7 |
| Storage stability test (MPa) | Bovine teeth enamel | 0.0 | 2.7 | 3.6 | 10.1 | 6.0 | 11.5 |
| | Bovine teeth dentine | 0.0 | 0.9 | 3.0 | 2.5 | 5.0 | 8.5 |

The adhesive strength of the dental adhesive compositions of Comparative Examples 9 through 12 listed in Table 6 are lower than that of the dental adhesive composition of Embodiment 1 listed in Table 1 on the whole. This reveals that a dental adhesive composition with high adhesive strength and high storage stability cannot be obtained if any one of the essential compounding ingredients (a), (b), (c) and (e) of the invention is not included. Also, the adhesive strength of the dental adhesive compositions of Comparative Examples 13 and 14 listed in Table 6 is lower than the adhesive strength of the dental adhesive compositions of Embodiments 1 through 83 (see Tables 1 and 3 through 5). This is because the curing property (the mechanical strength and the water resistance of a cured substance) of the dental adhesive compositions of Comparative Examples 13 and 14 is poorer than that of the dental adhesive compositions of Embodiments 1 through 67.

INDUSTRIAL APPLICABILITY

The one-part dental adhesive composition according to the present invention exhibits high adhesive strength without performing etching processing and priming processing and has high storage stability, and hence is useful particularly as a one-step type dental adhesive composition.

The invention claimed is:

1. A one-part dental adhesive composition comprising:
   1 through 50 wt % of a hydrophobic acidic group-containing polymeric monomer (a);
   22.5 through 60 wt % of a water-soluble polymeric monomer (b);
   1 through 50 wt % of water (c);
   0.01 through 10 wt % of a photopolymerization initiator (d);
   0.01 through 10 wt % of an aromatic tertiary amine (e) having an electron-withdrawing group;
   5 through 60 wt % of a cross-linkable polymeric monomer (f); and
   a basic compound (g) for producing a water-soluble salt through a reaction with a part of said hydrophobic acidic group-containing polymeric monomer (a) in an amount for adjusting pH of a resultant liquid to 1.5 through 4.0.

2. The one-part dental adhesive composition according to claim 1,
   comprising said cross-linkable polymeric monomer (f) in a ratio of 25 through 60000 parts by weight based on 100 parts by weight of said basic compound (g).

3. The one-part dental adhesive composition according to claim 1,
   wherein said hydrophobic acidic group-containing polymeric monomer (a) is a (meth)acrylate-based polymeric monomer having, in one molecule, at least one univalent or bivalent phosphoric or pyrophosphoric group, and
   said basic compound (g) is an aromatic secondary amine or an aromatic tertiary amine for producing the water-soluble salt through the reaction with a part of said hydrophobic acidic group-containing polymeric monomer (a).

4. The one-part dental adhesive composition according to claim 1,
   wherein said hydrophobic acidic group-containing polymeric monomer (a) is a (meth)acrylate-based polymeric monomer having, in one molecule, at least one univalent or bivalent phosphoric or pyrophosphoric group, and
   said basic compound (g) is an aliphatic secondary amine or an aliphatic tertiary amine for producing the water-soluble salt through the reaction with a part of said hydrophobic acidic group-containing polymeric monomer (a).

5. The one-part dental adhesive composition according to claim 1,
   wherein said hydrophobic acidic group-containing polymeric monomer (a) is a (meth)acrylate-based polymeric monomer having, in one molecule, at least one univalent or bivalent phosphoric or pyrophosphoric group, and
   said basic compound (g) is an aliphatic secondary amine having a hydroxyl group or an aliphatic tertiary amine having a hydroxyl group for producing the water-soluble salt through the reaction with a part of said hydrophobic acidic group-containing polymeric monomer (a).

6. The one-part dental adhesive composition according to claim 1, further comprising a water-soluble volatile organic solvent (h).

7. The one-part dental adhesive composition according to claim 1, further comprising a filler (i).

8. The one-part dental adhesive composition of claim 1, comprising 30 through 60 wt % of said water-soluble polymeric monomer (b).

* * * * *